United States Patent [19]

Pawelek

[11] Patent Number: 4,695,449

[45] Date of Patent: * Sep. 22, 1987

[54] COMPOSITION AND METHOD FOR TREATMENT OF MELANOMAS

[75] Inventor: John M. Pawelek, Hamden, Conn.

[73] Assignee: Yale University, New Haven, Conn.

[*] Notice: The portion of the term of this patent subsequent to Apr. 2, 2002 has been disclaimed.

[21] Appl. No.: 480,402

[22] Filed: Mar. 30, 1983

[51] Int. Cl.$^4$ ..................... A61K 49/00; A61K 43/00
[52] U.S. Cl. .......................... 424/1.1; 424/9; 514/107; 514/110; 514/117
[58] Field of Search .................... 424/1.1, 9, 209, 211; 514/110, 114, 107

[56] References Cited

U.S. PATENT DOCUMENTS 4,508,706 4/1985 Pawelek .............................. 514/107

OTHER PUBLICATIONS

Wick et al, Science, 197 (1977), pp. 468–469.
Carmichael et al, from *New Technologies in Tumor Localization and Radioimmuno Assay*, ed. Croll et al, J. Wiley & Sons (1974), pp. 193–202.
Gupta, from *Nuclear Medicine and Biology Advances*, vol. 3, Ed. C. Raynaud, Pergamon Press (1983), pp. 2997–3001.
Skromne-Kadlubik et al, from *Nuclear Medicine and Biology Advances*, vol. 1, Ed. C. Raynaud, Pergamon Press (1983), pp. 144–146.
Denardo et al, from *Nuclear Medicine and Biology Advances*, vol. 1, Ed. C. Raynaud, Pergamon Press (1983), pp. 182–185.
Mitsubishi Petrochemical Co., Ltd., Chem. Abstracts, vol. 94 (1981), #77035p.
Stringer et al, Chem. Abstracts, vol. 82 (1975), #132723r.

*Primary Examiner*—Christine M. Nucker
*Attorney, Agent, or Firm*—Lackenbach, Siegel, Marzullo & Aronson

[57] ABSTRACT

A composition and method for the treatment of melanomas in human beings wherein the composition comprises at least one O-phosphorylated derivative of 3-(3,4-dihydroxy)phenylalanine.

12 Claims, No Drawings

COMPOSITION AND METHOD FOR TREATMENT OF MELANOMAS

This invention was made with Government support under Grant Nos. 5RO1 CA 04679 and BRSG RR 05358 awarded by NIH. The Government has certain rights in the invention.

FIELD OF THE INVENTION

This invention relates to the treatment of melanomas in human beings. More particularly it relates to a composition useful in the treatment of melanomas comprising an O-phosphorylated derivative of 3-(3,4-dihydroxy)phenyl-L-alanine (hereafter "DOPA") which is selectively taken up by melanin synthasizing cells, such as melanomas, wherein the phosphorus is the $^{32}P$ isotope and a method for treating patients suffering form melanomas with said composition.

BACKGROUND OF THE INVENTION

Melanoma is a cancer resulting from the abnormal proliferation and spread (metastasis) of pigment cells (melanocytes) in the skin. The disease is related, to a certain extent, to exposure to UV radiation, e.g., sunlight. In the U.S. about 2% of all cancer deaths (about 10,000/yr.) may be attributed to melanomas. In the past twenty years the frequency of deaths attributed to melanomas has about doubled.

The usual treatment for melanoma is a complete surgical excision of the melanoma before the onset of metastasis. Once metastasis has occurred there is no cure and the disease is considered terminal.

It has been shown that in humans the cells that synthesize melanin, such as melanoma cells, selectively take up and use 3-(3,4-dihydroxy)phenyl-L-alanine (L-DOPA) as a substrate which is converted in the presence of specialized enzyme systems into melanin.

It is well known that inorganic phosphate is necessary for the synthesis of DNA and is essential for cell division. When $^{32}P$ is incorporated into the DNA of dividing cells it destroys them by causing scission in the DNA. Polycythemia, a disorder involving abnormal division of the red blood cells, can be cured by administration, to the patient, of $^{32}P$. However, the dosages of $^{32}P$ required for the destruction of most cancerous cells is high and causes undesirable side effects.

In accordance with the invention there is provided a composition for treatment of melanomas without the aforementioned concomitant deleterious effects.

SUMMARY

It is an object of the invention to provide a composition useful in the treatment of melanomas comprising an O-phosphorylated derivative of DOPA wherein the P comprises $^{32}P$.

It is another object of the invention to provide a treatment for melanoma comprising administration to a patient suffering from melanoma of a composition comprising an admixture of (a) at least one O-phosphorylated derivative of DOPA and (b) a pharmaceutically acceptable carrier.

Other objects of the invention will be apparent from the detailed description of the invention and the claim.

DETAILED DESCRIPTION OF THE INVENTION

In accordance with this invention there is provided a composition useful in the treatment of melanomas in human beings.

Thus, in accordance with one embodiment of this invention there is provided a composition useful for treatment of melanomas in human beings comprising at least one O-phosphorylated derivative of DOPA (hereafter "PD") of the general formula I

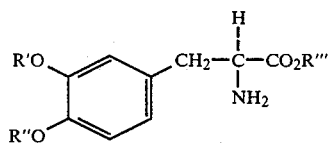

wherein R' and R" are each hydrogen or

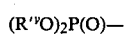

or R' and R" together represent

wherein R'' and R''' each represent hydrogen or a pharmaceutically acceptable cation and P is $^{32}P$ with the provisos that R' and R" cannot simultaneously be hydrogen. The formulae used throughout this application are not meant to depict any specific stereoisomeric forms.

The PD may be prepared from any of the stereoisomeric forms of DOPA, i.e., D-, L- and racemic. The most preferred form of DOPA to be used preparing the PDs of the invention is L-DOPA.

The above O-phosphorylated derivatives of DOPA are prepared by known methods using $^{32}P$ labeled starting materials. Thus, the DOPA derivatives may be prepared by treating DOPA with phosphorus oxychloride, a mixture of phosphoric acid and phosphorus pentoxide or pentasulfide, or polyphosphoric acid wherein the phosphorus in the phosphorylating compounds is $^{32}P$.

A preferred method for preparing the DOPA derivatives for use in accordance with the invention is by treating DOPA with a mixture of $^{32}P$ enriched $P_2O_5$ and phosphoric acid.

Preferred DOPA derivatives are those of formula II to V below;

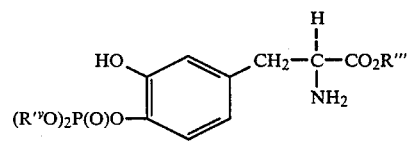

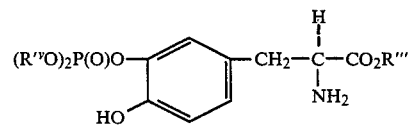

-continued

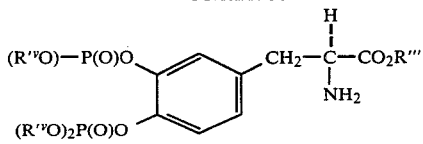

and

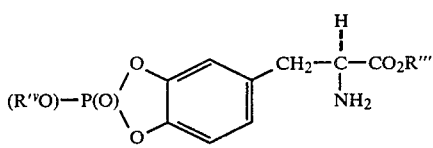

In accordance with yet another embodiment of the invention there is provided a composition for use in treating human melanomas comprising an admixture of (a) an effective amount of at least one of the O-phosphorylated derivatives of DOPA described above and (b) a pharmaceutically acceptable carrier.

Pharmaceutically acceptable carriers are known in the art and include distilled water and physiological saline solution.

If desired the composition according to the invention may also comprise at least one additive selected from the group consisting of acidity regulators, preservatives, chelating agents and the like.

The acidity regulators are pharmaceutically accepted buffers, acids and bases which will cause the pH of the composition to be one which can be tolerated by the patient. Such materials are known, per se, and will not be discussed further.

As the compositions of the instant invention are good growth media it is sometimes desirable to add preservatives such as bacteriostats, and the like, which are well known in the art.

The DOPA derivatives of the instant invention may be deactivated by easily oxidizable or reducible cations such as those of copper and iron. It is, therefore, sometimes desirable to add chelating agents, such as EDTA, to the composition of the invention.

The cations useful in accordance with the invention are monovalent and polyvalent cations which are not easily reduced or oxidized such as those from triethanolamine, tris(hydroxymethyl)aminomethane, sodium, potassium, calcium and magnesium, and the like. Preferred cations for use in accordance with the invention are those derived from triethanolamine and ... (hydroxymethyl)aminomethane and sodium or potassium.

According to yet another embodiment of the invention there is provided a method for treating a patient suffering from melanoma comprising the step of administering to said patient a composition comprising an admixture of (a) an effective amount of at least one of the O-phosphorylated DOPA derivatives described above. and (b) A pharmaceutically acceptable carrier.

The pharmaceutically acceptable carriers are known in the art and will not be discussed further.

The daily dosages used are such as to provide about 3-5 milicuries of $^{32}P$ for an adult. The actual dosage, which would also depend on the patient's weight, would have to be determined for each patient.

The composition, in accordance with this method, may be administered either parenterally or orally. Intravenous administration is the preferred technique.

The composition of the instant invention may also be used to treat other cancers such as neuoblastoma and pheochrocytoma since cells of these tumors utilize DOPA as an important metabolite.

In many instances the non-radioactive forms of the above DOPA derivatives will also be effective in treating melanomas and other cancers in which DOPA is an important metabolite.

I claim:

1. A composition useful in the treatment of melanomas in human beings comprising at least one O-phosphorylated derivative of DOPA of the general formula I

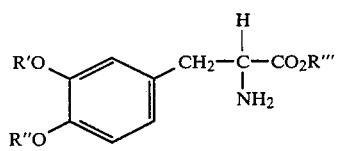

wherein R' and R" are each hydrogen or (R'"O)$_2$P(O)— or R' and R" together represent (R'"O)P(O)

wherein R'$^v$ and R'" each represent hydrogen or a pharmaceutically acceptable cation and P is $^{32}P$ with the provisos that R' and R" cannot simultaneously be hydrogen.

2. The composition according to claim 1, wherein the DOPA derivative has been prepared from L-DOPA.

3. The composition according to claim 2, wherein the DOPA derivative is

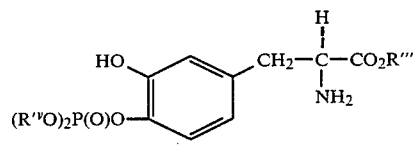

wherein R'" and R'$^v$ are as defined above.

4. The composition according to claim 2, wherein the DOPA derivative is

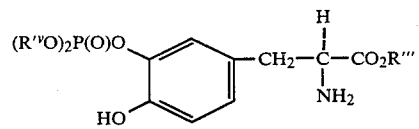

wherein R'" and R'$^v$ are as defined above.

5. The composition according to claim 2, wherein the DOPA derivative is

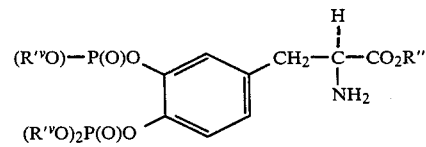

wherein R''' and R'$^v$ are as defined above.

6. The composition according to claim 2, wherein the DOPA derivative is

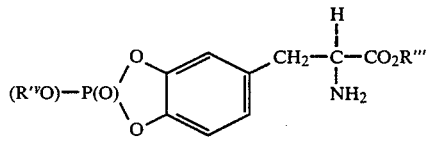

wherein R''' and R'$^v$ are as defined above.

7. A composition for the treatment of melanomas in human beings comprising an admixture of (a) an effective amount of at least one O-phosphorylated derivative of DOPA of the general formula I

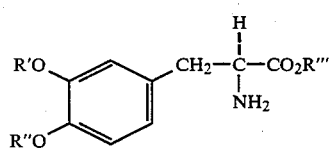

wherein R' and R'' are each hydrogen or (R'''O)$_2$P(O)— or R' and R'' together represent (R'''O)P(O)

wherein R'$^v$ and R''' each represent hydrogen or a pharmaceutically acceptable cation and P is $^{32}$P with the provisos that R' and R'' cannot simultaneously be hydrogen.

(b) a pharmaceutically acceptable carrier.

8. The composition according to claim 7, wherein the DOPA derivative is

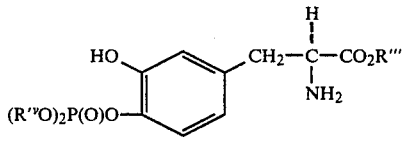

wherein R''' and R'$^v$ are as defined above.

9. The composition according to claim 7, wherein the DOPA derivative is

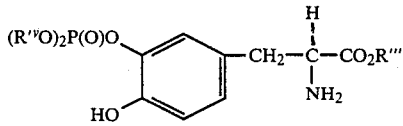

wherein R''' and R'$^v$ are as defined above.

10. The composition according to claim 7, wherein the DOPA derivative is

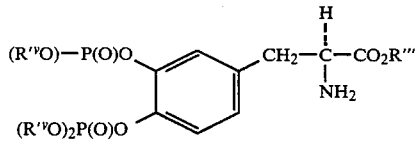

wherein R''' and R'$^v$ are as defined above.

11. The composition according to claim 7, wherein the DOPA derivative is

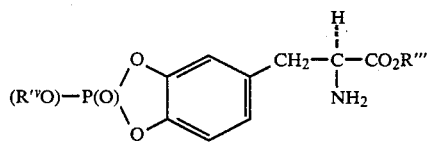

wherein R''' and R'$^v$ are as defined above.

12. A composition for the treatment of melanomas in human beings comprising an admixture of (a) an effective amount of

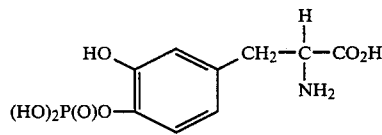

wherein P' is $^{32}$P; and (b) a pharmaceutically acceptable carrier.

* * * * *